United States Patent [19]

Kim et al.

[11] 4,127,593
[45] Nov. 28, 1978

[54] EPICHLOROHYDRIN PURIFICATION PROCESS

[75] Inventors: Leo Kim; Sunny C. Tang, both of Houston, Tex.

[73] Assignee: Shell Oil Company, Houston, Tex.

[21] Appl. No.: 873,312

[22] Filed: Jan. 30, 1978

[51] Int. Cl.² ........................................... C07D 301/32
[52] U.S. Cl. ............................................... 260/348.37
[58] Field of Search .................................. 260/348.37

Primary Examiner—Norma S. Milestone

[57] ABSTRACT

2,3-Butanedione impurity is removed from epichlorohydrin by contacting the impurity containing epichlorohydrin with a macroreticular poly(t-butyl acrylate) resin having a pore volume of about 0.5 ml/ml, an average pore diameter of about 90 angstroms and a surface area of about 450 m²/gm.

3 Claims, No Drawings

EPICHLOROHYDRIN PURIFICATION PROCESS

BACKGROUND OF THE INVENTION

1. Field of the Invention

This invention relates to a method of purifying epichlorohydrin by contact with a polymeric adsorbent.

2. Background of the Invention

In the commercial production of epichlorohydrin, small amounts of impurities are frequently present in the product stream that will degrade the product, causing it to be off specification. One of these impurities is 2,3-butanedione which is a color body which when present in epichlorohydrin causes it to have an undesirable greenish tint. A simple and inexpensive process for removing the impurity from the epichlorohydrin product without causing a significant loss in the epoxide value of the product would be very desirable.

SUMMARY OF THE INVENTION 2,3-Butanedione is removed from product epichlorohydrin by contacting the epichlorohydrin with a macroreticular poly(t-butyl acrylate) adsorbent resin having a pore volume between about 0.48 and 0.57 ml/ml, an average pore diameter between about 80 and about 100 angstroms and a surface area between about 400 to about 500 square meters/gm. The poly(t-butyl acrylate) resin of this invention is superior to other resins such as styrene-divinylbenzene and to resins having differing surface areas and pore diameters.

DESCRIPTION OF THE PREFERRED EMBODIMENTS

The resins used in this invention are macroreticular poly(t-butyl acrylate) resins having a porosity (milliliter of pore/milliliter of dried resin) between about 0.48 and about 0.57 and preferably between about 0.50 to about 0.55; a surface area between about 400 to about 500 square meters per gram (of dried resin) and preferably between about 425 to about 475 square meters per gram; and an average pore diameter (of the dried resin) between about 80 to about 100 angstroms and preferably between about 85 to about 95 angstroms.

The resins of the invention are contacted with the epichlorohydrin to be purified in either a batch process or a continuous or fixed-bed process. When a batch process is utilized, the resin is mixed with the epichlorohydrin and allowed to remain in contact therewith for about 0.01 to about 10 hours, preferably from about 0.1 to about 1 hours, and then separated by conventional means, e.g., filtration or centrifugation. In a continuous process the epichlorohydrin is preferably passed through a fixed bed of resin at liquid hourly space velocities ranging from about 0.1 to about 100 hours$^{-1}$, and preferably from about 0.5 to about 2.5 hours$^{-1}$. Temperatures of contact are not critical and are determined by the temperature stability of the resin and the freezing point of the epichlorohydrin. Temperatures are between about $-25°$ C. and about $150°$ C.

The process of this invention will be further described by the following illustrative embodiments which are provided for illustration and are not to be construed as limiting the invention.

ILLUSTRATIVE EMBODIMENTS

A series of resins (50 gram portions) shown in Table I were washed with 500 ml of deionized water, 250 ml of reagent grade methanol, 500 ml of reagent grade acetone and then dried in a vacuum at about 50° C. overnight.

Table 1

| Source | Type | Porosity | Surface Area $m^2$/gm | Avg. Pore Diameter Angstroms |
|---|---|---|---|---|
| Resin #1 Rohm and Haas XAD-4 | Polystyrene | 0.51 | 780 | 50 |
| Resin #2 Rohm and Haas XAD-7 | Acrylic ester | 0.55 | 450 | 90 |
| Resin #3 Rohm and Haas XAD-8 | Acrylic ester | 0.52 | 140 | 235 |

A 29.5 × 7/16 inch glass column was packed (wet) with 20 cc of the appropriate resin prepared as above. Epichlorohydrin was allowed to pass through the resin by gravity at a liquid hourly space velocity of approximately 1–2 hours$^{-1}$. After 20 ml of epichlorohydrin had passed through the column, the next 50 ml sample of epichlorohydrin was collected. The color index of the material was measured using ASTM D-1209-69. The concentration of 2,3-butanedione was measured with UV light absorptions in comparison with standard samples of 2,3-butanedione of known concentration. The epoxide values were measured by NaI-isopropyl alcohol-acetic acid peroxide titration method. The results are shown in Table II.

Table II

| | Color Index | 2,3-Butanedione, ppm | Epoxide Value, %w |
|---|---|---|---|
| No resin used | 40–50 | 25 | 99.0 |
| Resin #1 | 25–30 | 20 | 98.9 |
| Resin #2 | 15–20 | 0 | 99.1 |
| Resin #3 | 25–30 | 15 | 98.9 |

Thus it can be seen that the resin of this invention (Resin #2) significantly lowers the color index, removes substantially all of the 2,3-butanedione impurity without adversely affecting the epoxide value whereas other similar resins do not do so.

What is claimed is:

1. The process of removing 2,3-butanedione impurity from epichlorohydrin which comprises contacting said epichlorohydrin with a macroreticular poly(t-butyl acrylate) adsorbent resin having a pore volume between about 0.48 and about 0.57, an average pore diameter between about 80 and about 100 angstroms and a surface area between about 400 to about 500 square meters per gram.

2. The process of claim 1 wherein the resin has a pore volume between about 0.50 and about 0.55, an average pore diameter between about 85 and about 95 angstroms and a surface area between about 425 to about 475 square meters per gram.

3. The process of claim 1 where the resin is contained in a fixed-bed and said epichlorohydrin is passed through said bed at a liquid hourly space velocity ranging between about 0.1 to about 100 hours$^{-1}$.

* * * * *